(12) United States Patent
Jung et al.

(10) Patent No.: US 8,965,480 B2
(45) Date of Patent: Feb. 24, 2015

(54) ARTERIAL BLOOD FLOW AND TRANSIT DELAY MEASUREMENT USING ARTERIAL SPIN LABELING

(75) Inventors: Youngkyoo Jung, Winston-Salem, NC (US); Kun Lu, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 185 days.

(21) Appl. No.: 13/641,458

(22) PCT Filed: Apr. 14, 2011

(86) PCT No.: PCT/US2011/032591
§ 371 (c)(1),
(2), (4) Date: Dec. 28, 2012

(87) PCT Pub. No.: WO2011/130581
PCT Pub. Date: Oct. 20, 2011

(65) Prior Publication Data
US 2013/0096418 A1    Apr. 18, 2013

Related U.S. Application Data

(60) Provisional application No. 61/324,173, filed on Apr. 14, 2010.

(51) Int. Cl.
*A61B 5/055* (2006.01)
*A61B 5/026* (2006.01)
*G01R 33/563* (2006.01)

(52) U.S. Cl.
CPC ........ *A61B 5/0263* (2013.01); *G01R 33/56366* (2013.01)
USPC ........................................................ 600/419

(58) Field of Classification Search
CPC .................................................. G01R 33/56366
USPC ............................................................ 600/419
See application file for complete search history.

(56) References Cited

U.S. PATENT DOCUMENTS 6,271,665 B1    8/2001    Berr et al.
6,564,080 B1    5/2003    Kimura
(Continued)

FOREIGN PATENT DOCUMENTS

JP      2005-305151 A    11/2005
WO      03/094725 A1     11/2003
(Continued)

OTHER PUBLICATIONS

Wang et al. ("Arterial Transit Time Imaging with Flow Encoding Arterial Spin Tagging (FEAST)", Magnetic Resonance in Medicine, 50:599-607, 2003).*
(Continued)

*Primary Examiner* — Jonathan Cwern
(74) *Attorney, Agent, or Firm* — Perkins Coie LLP

(57) ABSTRACT

Techniques and systems are disclosed for measuring arterial transit delay using pseudo-continuous arterial spin labeling (ASL) with variable TR and interleaved post-labeling delays. In one aspect, a magnetic resonance imaging method for measure arterial blood flow and transit delay using arterial spin labeling (ASL) includes applying an ASL pulse sequence. The ASL pulse sequence includes a pre-saturation pulse, and a labeling pulse. The method includes performing data acquisition to measure a transit delay, which represents a time needed for labeled blood to arrive in an imaging slice.

9 Claims, 8 Drawing Sheets

(56) References Cited

U.S. PATENT DOCUMENTS

| | | | |
|---|---|---|---|
| 7,587,233 | B2 | 9/2009 | Wong et al. |
| 8,195,274 | B2 | 6/2012 | Wong |
| 2004/0030240 | A1* | 2/2004 | Kimura .................. 600/420 |
| 2004/0044281 | A1 | 3/2004 | Jesberger et al. |
| 2004/0162483 | A1 | 8/2004 | Kimura |
| 2005/0277825 | A1 | 12/2005 | Wong et al. |
| 2005/0277828 | A1 | 12/2005 | Alsop |
| 2006/0100503 | A1 | 5/2006 | Takai et al. |
| 2006/0161060 | A1 | 7/2006 | Pai |
| 2006/0184007 | A1 | 8/2006 | Judd et al. |
| 2007/0282193 | A1 | 12/2007 | Brown |
| 2008/0269595 | A1 | 10/2008 | Wong |
| 2009/0088626 | A1 | 4/2009 | Sutton et al. |
| 2009/0245607 | A1* | 10/2009 | Sugiura .................. 382/131 |
| 2010/0030062 | A1 | 2/2010 | Bolar et al. |
| 2010/0240983 | A1 | 9/2010 | Jung et al. |
| 2012/0268126 | A1 | 10/2012 | Guo et al. |
| 2012/0271157 | A1 | 10/2012 | Wong et al. |

FOREIGN PATENT DOCUMENTS

| | | |
|---|---|---|
| WO | 03/094728 A1 | 11/2003 |
| WO | 2010/108161 A2 | 9/2010 |
| WO | 2012/145687 A2 | 10/2012 |
| WO | 2012/145765 A2 | 10/2012 |

OTHER PUBLICATIONS

Alsop, D.C., et al., "Reduced transit-time sensitivity in noninvasive magnetic resonance imaging of human cerebral blood flow," Journal of Cerebral Blood Flow and Metabolism, 16(6):1236-1249, Nov. 1996.

Brookes, M.J., et al, "Noninvasive measurement of arterial cerebral blood volume using look-locker EPI and arterial spin labeling," Magnetic Resonance in Medicine, 58(1):41-54, Jul. 2007.

Buxton, R.B., et al., "A general kinetic model for quantitative perfusion imaging with arterial spin labeling," Magnetic Resonance in Medicine, 40(3):383-396, Sep. 1998.

Dai, W., et al., "Continuous Flow-Driven Inversion for Arterial Spin Labeling Using Pulsed Radio Frequency and Gradient Fields," Magnetic Resonance in Medicine, 60(6):1488-1497, Dec. 2008.

Davies, N.P., et al., "Selective arterial spin labeling (SASL): perfusion territory mapping of selected feeding arteries tagged using two-dimensional radiofrequency pulses," Magnetic Resonance in Medicine, 49(6):1133-1142, Jun. 2003.

Detre, J.A., et al., "Perfusion imaging," Magnetic Resonance in Medicine, 23(1):37-45, Jan. 1992.

Detre, J.A., et al., "Noninvasive Perfusion MR Imaging Using Spin Labeling Arterial Water," Chapter 15, Part V in Diffusion and Perfusion: Magnetic Resonance Imaging: Applications to Functional MRI (D. Le Bihan, Ed.), p. 296-305, Raven Press, New York, 1995.

Dixon, W.T., et al., "Projection angiograms of blood labeled by adiabatic fast passage," Magnetic Resonance in Medicine, 3(3):454-462, Jun. 1986.

Duyn, J.H., et al., "Simple correction method for k-space trajectory deviations in MRI," Journal of Magnetic Resonance, 132(1):150-153, May 1998.

Edelman, R.R. et al "Qualitative mapping of cerebral blood flow and functional localization with echo-planar MR imaging and signal targeting with alternating radio frequency," Radiology, 192(2):513-520, Aug. 1994.

Garcia, D.M., et al., "Pseudo-continuous flow driven adiabatic inversion for arterial spin labeling," Proceedings 13th Scientific Meeting, International Society for Magnetic Resonance in Medicine, p. 37, (2005).

Garwood, M., et al., "Advances in Magnetic Resonance—The Return of the Frequency Sweep: Designing Adiabatic Pulses for Contemporary NMR," Journal of Magnetic Resonance, 153(2):155-177, Dec. 2001.

Garwood, M., et al., "Symmetric Pulses to Induce Arbitrary Flip Angles with Compensation for RF Inhomogeneity and Resonance Offsets," Journal of Magnetic Resonance, 94(3):511-525, Oct. 1991.

Gunther, M., "Efficient visualization of vascular territories in the human brain by cycled arterial spin labeling MRI," Magnetic Resonance in Medicine, 56(3):671-675, Sep. 2006.

Gunther, M., et al. "Single-shot 3D imaging techniques improve arterial spin labeling perfusion measurements," Magnetic Resonance in Medicine, 54(2):491-498, Aug. 2005.

Guo, J., et al., "Imaging of Oxygen Extraction Fraction Using Velocity Selective Excitation with Arterial Nulling (VSEAN)," Proceedings of the International Society for Magnetic Resonance in Medicine,18:4057, (2010).

Hendrikse, J., "Flow territory mapping of the cerebral arteries with regional perfusion MRI," Stroke, 35(4):882-887, Apr. 2004.

Hennig, et al., "Hyperechoes," Magnetic Resonance in Medicine, 46(1):6-12, Jul. 2001.

International Search Report and Written Opinion mailed on Dec. 21, 2011 for International Application No. PCT/US2011/032591, filed Apr. 14, 2011 (7 pages).

International Search Report and Written Opinion mailed on Nov. 30, 2012 for International Application No. PCT/US2012/034537, filed Apr. 20, 2012 (6 pages).

International Search Report and Written Opinion mailed on Nov. 30, 2012 for International Application No. PCT/US2012/034720, filed Apr. 23, 2012 (6 pages).

International Search Report and Written Opinion mailed on Oct. 22, 2010 for International Application No. PCT/US2010/028068, filed Mar. 19, 2010 (7 pages).

International Search Report and Written Opinion mailed on Sep. 15, 2003 for International Application No. PCT/US03/14978, filed May 13, 2003 (3 pages).

Jung, Y., et al., "Multi-phase pseudo-continuous arterial spin labeling (MP PCASL): Robust PCASL method for CBF quantification," Proceedings 17th Scientific Meeting, International Society for Magnetic Resonance in Medicine, p. 622, (2009).

Jung, Y., et al., "Multiphase pseudocontinuous arterial spin labeling (MP-PCASL) for robust quantification of cerebral blood flow," Magnetic Resonance in Medicine, 64(3):799-810, Sep. 2010.

Jung, Y., et al., "Pseudo-continuous arterial spin labeling with optimized tagging efficiency for quantitative ASL fMRI," Proceedings 17th Scientific Meeting, International Society for Magnetic Resonance in Medicine, p. 1578, (2009).

Kim, S.G., "Quantification of relative cerebral blood flow change by flow-sensitive alternating inversion recovery (FAIR) technique: Application to functional mapping," Magnetic Resonance in Medicine, 34(3):293-301, Sep. 1995.

Kim, S.G., et al., "Perfusion imaging by a flow-sensitive alternating inversion recovery (FAIR) technique: Application to functional brain imaging," Magnetic Resonance in Medicine, 37(3):425-435, Mar. 1997.

Kwong, K.K. et al., "Perfusion MR imaging," Proceedings of the Society of Magnetic Resonance, vol. 2, Second Meeting, Aug. 6-12, 1994, San Francisco, California, p. 1005.

Lagarias, J.C., et al., "Convergence properties of the nelder-mead simplex method in low dimensions," SIAM Journal on Optimization, 9(1):112-147, (1998).

Liu, T.T., et al., "A signal processing model for arterial spin labeling functional MRI," NeuroImage, 24(1):207-215, Jan. 2005.

Lu, K., et al., "Regional white matter perfusion measurement using an optimized pseudo-continuous ASL MRI," Proceedings 17th Scientific Meeting, International Society for Magnetic Resonance in Medicine, p. 1521, (2009).

Luh, W.M., et al, "Pseudo-continuous Arterial Spin Labeling at 7T," Proceedings 16th Scientific Meeting, International Society for Magnetic Resonance in Medicine, p. 3339, (2008).

Luh, W.M., et al., "QUIPSS II with thin-slice T1 Periodic Saturation: A Method for Improving Accuracy of Quantitative Perfusion Imaging Using Pulsed Arterial Spin Labeling," Magnetic Resonance in Medicine, 41(6):1246-1254, Jun. 1999.

Mildner, T., et al., "Continuous arterial spin labeling at the human common carotid artery: the influence of transit times," NMR in Biomedicine, 18(1):19-23, Feb. 2005.

(56) References Cited

OTHER PUBLICATIONS

Norris, D.G., et al., "Velocity Selective Radiofrequency Pulse Trains", Journal of Magnetic Resonance, 137(1):231-236, Mar. 1999.

Paley, R.E.A.C., "On Orthogonal Matrices," Journal of Mathematics and Physics, 12:311-320, (1932-1933).

Parry, A. & P.M. Matthews, "Functional magnetic resonance imaging (fMRI): A 'window' into the brain," Oxford University, Centre for Functional Magnetic Resonance Imaging of the Brain (2002), 42 pages, Web site: http://www.fmrib.ox.ac.uk/fmri_intro/fmri_intro.htm [originally accessed on Aug. 20, 2003].

Sutton, B.P., et al., "Fast, iterative image reconstruction for MRI in the presence of field inhomogeneities," IEEE Transactions on Medical Imaging, 22(2):178-188, Feb. 2003.

Trampel, R., et al., "Efficiency of Flow-Driven Adiabatic Spin Inversion Under Realistic Experimental Conditions: A Computer Simulation," Magnetic Resonance in Medicine, 51(6):1187-1193, Jun. 2004.

Van Gelderen, P., et al., "Pittfalls of Mri measurement of white matter perfusion based on arterial spin labeling," Magnetic Resonance in Medicine, 59(4):788-795, Apr. 2008.

Wang, J., et al., "Amplitude-modulated continuous arterial spin-labeling 3.0-T perfusion MR imaging with a single coil: feasibility study," Radiology, 235(1):218-228, Apr. 2005.

Werner, R., et al., "Continuous artery-selective spin labeling (CASSL)," Magnetic Resonance in Medicine, 53(5):1006-1012, May 2005.

Williams, D.S., et al., "Magnetic resonance imaging of perfusion using spin inversion of arterial water," Proceedings of the National Academy of Sciences of the United States of America, 89(1):212-216, Jan. 1992.

Wong, E.C., "Vessel-encoded arterial spin-labeling using pseudocontinuous tagging," Magnetic Resonance in Medicine, 58(6):1086-1091, Dec. 2007.

Wong, E.C., "Vessel Encoded Arterial Spin Labeling Using Pseudo-Continuous Tagging," Proceedings of the International Society for Magnetic Resonance in Medicine, 14:668, (2006).

Wong, E.C., et al., "Blind detection of vascular sources and territories using random vessel encoded arterial spin labeling," Magnetic Resonance Materials in Physics, Biology and Medicine, 25(2):95-101, Apr. 2012.

Wong, E.C., et al., "Implementation of quantitative perfusion imaging techniques for functional brain mapping using pulsed arterial spin labeling," NMR in Biomedicine, 10(4-5):237-249, Jun.-Aug. 1997.

Wong, E.C., et al., "Quantitative imaging of perfusion using a single subtraction (Quipss and Quipss Ii)," Magnetic Resonance in Medicine, 39(5):702-708, May 1998.

Wong, E.C., et al., "Velocity-selective arterial spin labeling," Magnetic Resonance in Medicine, 55(6):1334-1341, Jun. 2006.

Wong, E.C., et al., "Velocity Selective Arterial Spin Labeling using an Adiabatic Hyperecho Pulse Train," Proceedings of the International Society for Magnetic Resonance in Medicine, 11:2181, (2003).

Wong, E.C., et al., "Velocity Selective Arterial Spin Labeling," Proceedings of the International Society for Magnetic Resonance in Medicine, 10:621, (2002).

Wu, W.C., et al., "A theoretical and experimental investigation of the tagging efficiency of pseudocontinuous arterial spin labeling," Magnetic Resonance in Medicine, 58(5):1020-1027, Nov. 2007.

Wu, W.C., et al., "The Effects of Flow Dispersion and Cardiac Pulsation in Arterial Spin Labeling," IEEE Transactions on Medical Imaging, 26(1):84-92, Jan. 2007.

Zaharchuk, G. et al., "Multislice perfusion and perfusion territory imaging in humans with separate label and image coils," Magnetic Resonance in Medicine, 41(6):1093-1098, Jun. 1999.

Zimine, I., et al., "Dual vessel arterial spin labeling scheme for regional perfusion imaging," Magnetic Resonance in Medicine, 56(5):1140-1144, Nov. 2006.

* cited by examiner

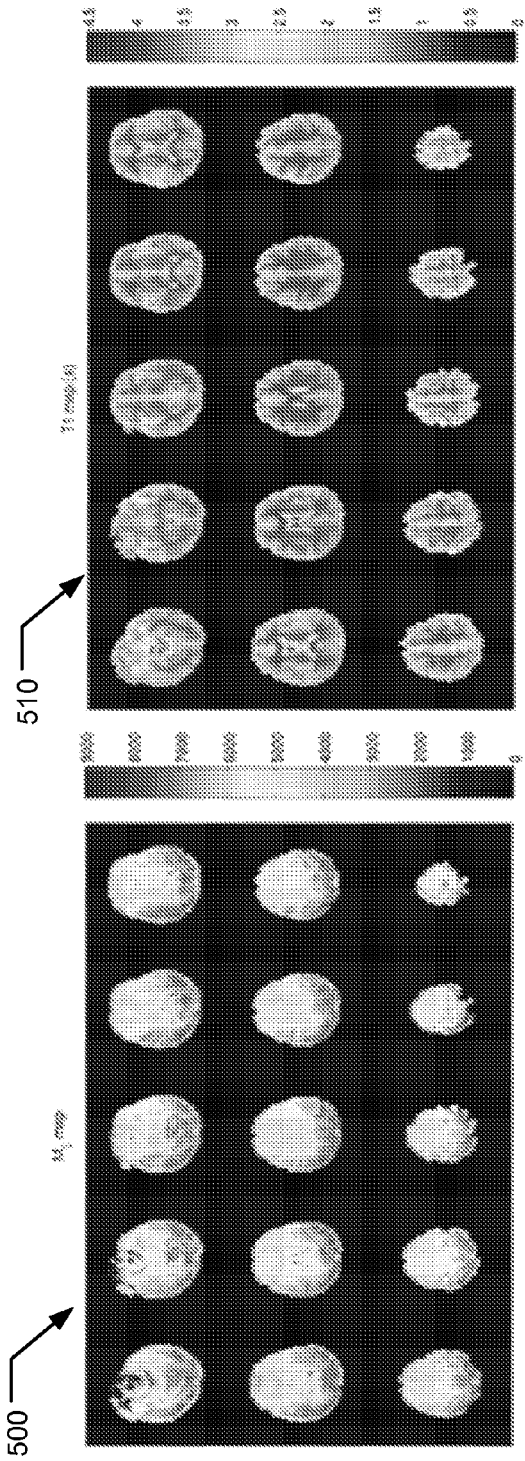
FIG. 5A
FIG. 5B
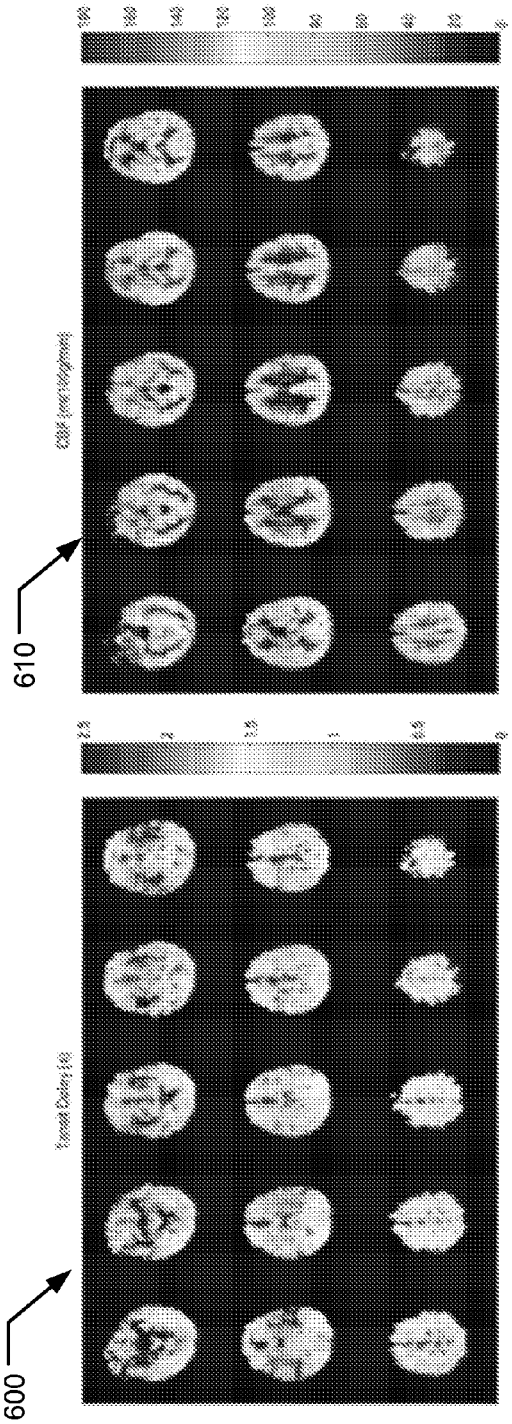
FIG. 6A
FIG. 6B

ARTERIAL BLOOD FLOW AND TRANSIT DELAY MEASUREMENT USING ARTERIAL SPIN LABELING

CROSS REFERENCE TO RELATED APPLICATIONS

This document is a 35 USC 371 National Stage application of International Application No. PCT/US2011/032591 filed Apr. 14, 2011, which claims the benefit of U.S. Provisional Patent Application No. 61/324,173, filed Apr. 14, 2010, entitled "ARTERIAL BLOOD FLOW AND TRANSIT DELAY MEASUREMENT USING ARTERIAL SPIN LABELING". The entire content of the before-mentioned patent applications is incorporated by reference as part of the disclosure of this application.

BACKGROUND

This application relates to devices and techniques that use magnetic resonance imaging (MRI) techniques.

Imaging through MRI techniques is well known and has been widely applied in imaging applications in medical, biological and other fields. In essence, a typical MRI technique produces an image of a selected body part of an object under examination by manipulating the magnetic spins in a body part and processing measured responses from the magnetic spins. MRI systems may include hardware to generate different magnetic fields for imaging, including a static magnetic field along a z-direction to polarize the magnetic spins, gradient fields along mutually orthogonal x, y, or z directions to spatially select a body part for imaging, and an RF magnetic field to manipulate the spins.

Currently, transit delays in an arterial spin labeling (ASL) experiment, such as Proximal Inversion with a Control for Off-Resonance Effect (PICORE), Flow-sensitive Alternating Inversion Recovery (FAIR), and pulsed continuous ASL (PCASL), refer to the time required for the labeled blood to arrive in the imaging slice. Knowledge of the transit delays is very important for conducting ASL experiments. Transit delay measurements include a series of separate ASL experiments acquired at several different post-labeling delays (PLD). Additional scans are usually needed to map T1 and blood magnetization (M0) for core blood flow (CBF) quantification. Such measurements are usually time-consuming and can be formidable overheads for ASL studies. The time requirement also makes the measurements highly sensitive to motion.

SUMMARY

Techniques and structures and apparatus are disclosed for measuring arterial blood flow and transit delay using arterial spin labeling (ASL).

The subject matter described in this specification potentially can provide one or more of the following advantages. The described transit delay measurement method includes variable repetition time (TR) and interleaved post labeling delay (PLD). The variable TR can enable reduction of scan time and the interleaved PLD can reduce sensitivity to motion artifact in the estimation of arterial blood flow and transit delay.

BRIEF DESCRIPTION OF THE DRAWINGS

FIG. 5A shows an exemplary estimated M0 from the central 15 slices out of 20.

FIG. 5B shows an exemplary estimated T1 from the central 15 slices out of 20.

FIGS. 6A and 6B show exemplary estimated transit delay and CBF respectively.

Like reference symbols and designations in the various drawings indicate like elements.

DETAILED DESCRIPTION

Figure 1:
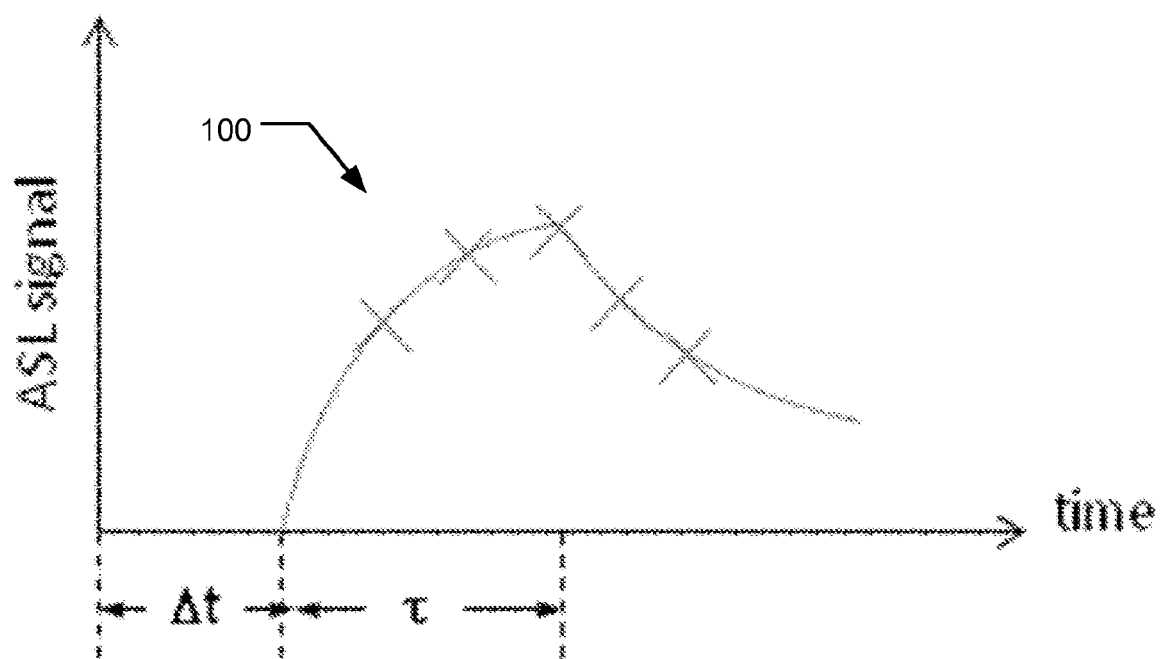
FIG. 1 shows an exemplary ASL signal curve described by Eq. 1.

The techniques, structures and apparatus described in this application can be used to measure arterial blood flow and transit delay using arterial spin labeling (ASL). The described transit delay measurement method can include variable repetition time (TR) and interleaved post labeling delay (PLD). The variable TR can allow reduction of scan time and the interleaved PLD can reduce sensitivity to motion artifact in the estimation of arterial blood flow and transit delay.

The Arterial Spin Labeling or Tagging (ASL or AST) methods can measure blood perfusion by using subtraction of tag and control. Sensitivity to transit delay (or transit time) and reliance on calibration scans, such as spin-lattice relation time (T1), blood magnetization, and coil inhomogeneity measurements can result in transit delay measurement that is time-consuming and sensitive to subject motion. The techniques described in this document can significantly reduce the scan time and the sensitivity to subject motion. In addition the need for additional calibration scans is eliminated.

ASL Signal Model

PCASL is utilized due to its higher SNR. But the same technique can be applied to pulsed ASL, such as PICORE and FAIR. The signal equation corresponding the acquisition timing is described in Eq 1.

$$\Delta M(t) = 0 \qquad 0 < t < \Delta t \qquad \text{Eq. 1}$$
$$= 2 \cdot M_{0B} \cdot f \cdot T_1' \cdot \alpha \cdot e^{-\Delta t / T_{1b}} \cdot \quad \Delta t < t < \tau + \Delta t$$
$$(1 - e^{-(t - \Delta t)/T_1'})$$
$$= 2 \cdot M_{0B} \cdot f \cdot T_1' \cdot \alpha \cdot e^{-\Delta t / T_{1b}} \cdot \quad \tau + \Delta t < t$$
$$e^{-(t - \tau - \Delta t)/T_1'} \cdot (1 - e^{-\tau / T_1'})$$

Where $\Delta M(t)$ is the measured signal by subtraction of tag and control, $\Delta t$ is the transit delay, 2 is the tagging duration, $M_{0B}$ is the net magnetization of blood, f, is the arterial blood flow, $T_1'$ and $T_{1b}$ is the $T_1$ of the tissue and the blood, respectively, and a is the tagging efficiency.

Typical CBF quantification is processed under following assumptions:

1) $\tau+\Delta t<t$: The time of acquisition is later than the sum of the pulse width and the transit delay, i.e. the post labeling delay after the tagging pulse is longer than the transit delay.
2) $T_1'=T_{1b}$: The $T_1$ of tissue is same as the blood $T_1$.

For assumption 1, the post labeling delay should be longer than the transit delay, delay for blood to be delivered from the tagging location to the tissue. Even though the transit delay can be modulated by various physiologic and pathologic conditions, such as, disease condition, age, and gender, an assumed transit delay (~1 sec) is typically used. For tissues that have longer transit delays, an underestimation of CBF will occur. Assumption 2 neglects the difference of $T_1$ value between blood and tissue, which introduces errors in CBF estimates, especially in white matter where the difference is big. $T_1$ measurement is desired for accurate CBF estimation, but it increases scan time.

In addition to these assumptions, a separate scan for estimating $M_{0B}$ is required for the quantification, and another scan for estimating coil sensitivities is also needed for removing modulation due to non-uniformity of different coils.

Transit Delay Estimation

Transit delay measurement is key for providing accurate CBF estimation. The measured transit delay are also physiological and pathological indicators. The transit delay can be measured with multiple different PLDs. FIG. 1 describes the transit delay measurement with multiple points. The ASL signal is the signal difference between tag and control and the continuous curve represents the ASL signal from Eq. 1. The crosses on the curve are the measured time points at different PLDs. The actual timing of the measurement is $\tau$+PLD. CBF and $\Delta t$ can be estimated by a non-linear fitting process of the signal curve. FIG. 1 shows an ASL signal curve 100 described by Eq. 1. The collection of signals at multiple points (indicated by x) allows the estimation of transit delay ($\Delta t$) and blood flow.

Transit Delay Measurement

Figures 2A, 2B:
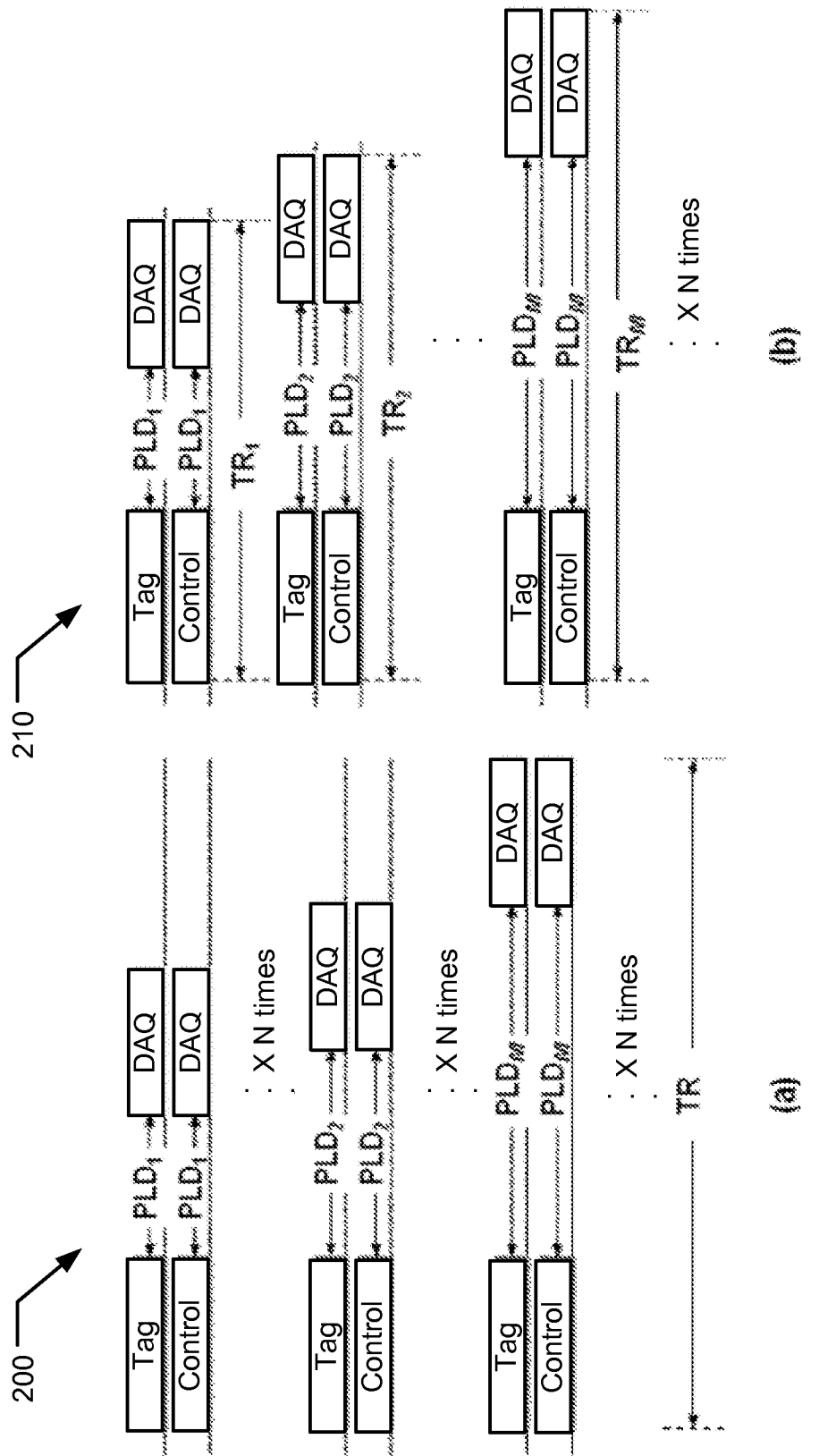
FIG. 2A shows an exemplary description of the conventional transit delay measurement.
FIG. 2B shows an exemplary description of the method described in this specification.

FIG. 2A shows an exemplary description of conventional transit delay measurement (200). FIG. 2B shows an exemplary description of a technique described in this document (210). ASL experiments use many averages to gain signal to noise ratio (SNR). Conventional transit delay methods acquire all the averages of N at one PLD before moving to the next PLD and the TR is fixed to the longest (FIG. 2A). The described techniques can acquire one tag/control pair for every PLD point and then moves to the next pair and it utilizes variable and minimum TR (FIG. 2B). In this configuration total scan time can be reduced by ~30% and it is less sensitive to subject motion. Such an acquisition scheme reduces the sensitivity to motion since head movement will be less likely to cause complete loss of one or more of the PLD points.

Pre-Saturation Pulse

Figure 3:
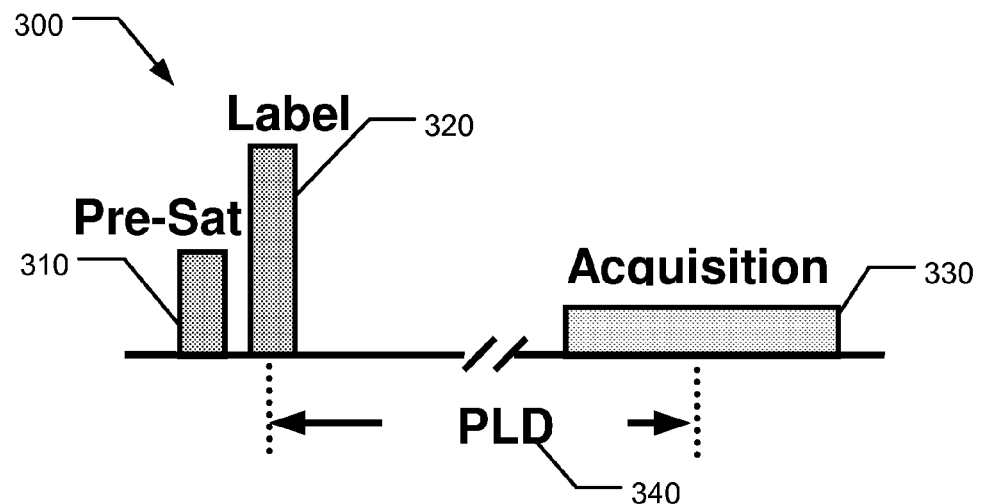
FIG. 3 shows an exemplary ASL pulse sequence including pre-saturation and labeling pulses.
Figure 4:
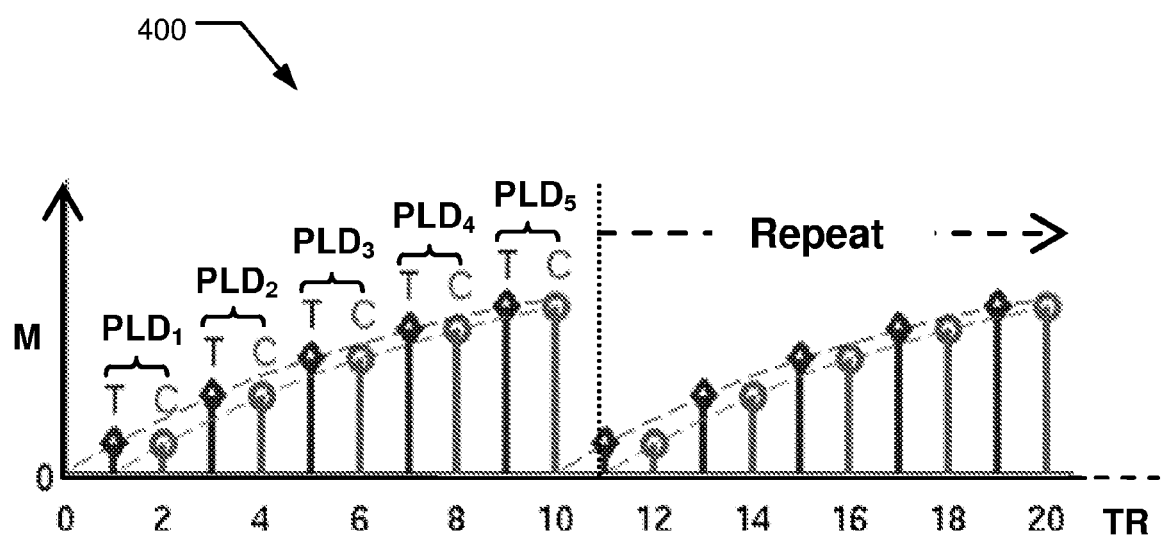
FIG. 4 shows an exemplary acquisition scheme for measuring transit delay.

The proposed method relies on the pre-saturation to saturate the imaging slice immediately before the labeling pulse (FIG. 3). FIG. 3 shows an exemplary ASL pulse sequence 300 including pre-saturation 310 and labeling 320 pulses. The time between labeling pulse and data acquisition 330 is the post labeling delay (PLD) 340. The pre-saturation pulse 310 causes the tissue signal to recover from zero at the beginning of each TR, which has the following results: 1) the tissue signal intensity is independent of TR, which means that shorter TR can be used for scans with short PLDs and TR increases as PLD does; 2) the tissue signal intensity at each PLD follows a saturation recovery curve determined by the tissue T1 (FIG. 4), allowing T1 and $M_0$ estimation without the need for additional scans. FIG. 4 shows an exemplary acquisition scheme 400 for measuring transit delay. T denotes tag (or label) and C denotes control. The tag and control image intensities follow a saturation recovery curve at different PLDs. Both these features can enable a reduction in scan time.

T1 And M0 Estimation

For the described techniques, it is not necessary to collect separate $T_1$ measurement because Tissue $T_1$ and $M_0$ can be estimated by the ASL data with different PLDs. The tag and control data at each PLD point are averaged to reduce the effect of inflow blood. And the all the averaged PLD points are fitted into Eq. 2 for the estimation of $T_1$ and $M_0$ $$S(t)=M_0(1-e^{-t/T_1}) \qquad \text{Eq. 2}$$

where t is the acquisition time after the pre-saturation, which is T+PLD.

Experimental Parameters

The acquisition scheme was implemented with an in-house ASL pulse sequence with variable PLD, variable TR capability and single shot spiral acquisition. Data was acquired on a healthy human subject on a General Electric (GE) Signa HDx 3.0 Tesla research scanner with a standard 8 channel head coil (GE, Waukesha, Wis.). An optimized pseudo-continuous ASL (PCASL) method was used with following parameters: labeling duration 1.0 sec, TE 3 ms, Variable TR (1.8–4.2 sec), 20 slices, 5 mm thick with no gap, FOV 22 cm, 64×64 matrix, 7 PLD points {0.2 0.6, 1.0, 1.4, 1.8, 2.2, 2.6 sec}, 10 pairs of Tag and control images at each PLD, total scan time 7 min.

FIG. 5A shows an estimated $M_0$ (500) from the central 15 slices out of 20. FIG. 5B shows an estimated $T_1$ (510) from the central 15 slices out of 20. Note that these are calculated from the collected data, and no separate calibration scans are needed.

FIGS. 6A and 6B show the estimated transit delay (600) and CBF (610) respectively.

The M0 and T1 values in FIGS. 5A and 5B were used for the quantification without the use of any separate calibration scans.

In another aspect, techniques, apparatus and systems are described for implementing arterial transit delay measurement using pseudo-continuous ASL with variable TR and interleaved post-labeling delays. Transit delays in an ASL experiment refer to the time required for the labeled blood to arrive in the imaging slice. Knowledge of the transit delays is very important for conducting ASL experiments. Transit delay measurements can include a series of separate ASL experiments acquired at several different post-labeling delays (PLD). The data can be then fitted to a mathematical model to obtain estimates of the transit delays. Additional scans are usually needed to map T1 and blood magnetization (M0) for CBF quantification. Such measurements are usually time-consuming and can be formidable overheads for ASL studies. The time requirement also makes the measurements highly sensitive to motion. The use of Look-Locker sampling or 3D imaging technique can improve the time efficiency. However, there are more direct ways to address the issue by simple modifications of the conventional method. Described herein is a modified method for measuring transit delay with shorter scan time and less motion sensitivity.

The described method uses the pre-saturation pulse 310 that is typically applied in ASL experiments to saturate the imaging slice immediately before the labeling pulse (see FIG. 3). As described above, the pre-saturation pulse 310 causes the tissue signal to recover from zero at the beginning of each TR, which has the following results: 1) the tissue signal intensity is independent of TR, which means that shorter TR can be used for scans with short PLDs and TR increases as PLD does; 2) the tissue signal intensity at each PLD follows a saturation recovery curve 400 determined by the tissue T1 (see FIG. 4), allowing T1 and M0 estimation without the need for additional scans. Both these features can enable a reduction in scan time. Additionally, ASL experiments require many averages to gain signal to noise ratio (SNR). Conventional transit delay methods acquire all the averages at one PLD before moving to the next PLD. Our method acquires one tag/control pair for every PLD point and then moves to the next pair (see FIG. 4). Such an acquisition scheme reduces the sensitivity to motion since head movement will be less likely to cause complete loss of one or more of the PLD points.

The described acquisition scheme was implemented with an in-house ASL pulse sequence with variable PLD, variable TR capability and single shot spiral acquisition. Data was acquired on a healthy human subject on a General Electric (GE) Signa HDx 3.0 Tesla research scanner with a standard 8 channel head coil (GE, Waukesha, Wis.). An optimized pseudo-continuous ASL (PCASL) method was used with following parameters: labeling duration 1.0 sec, TE 3 ms, Variable TR (1.8–4.2 sec), 20 slices, 5 mm thick with no gap, FOV 22 cm, 64×64 matrix, 7 PLD points {0.2 0.6, 1.0, 1.4, 1.8, 2.2, 2.6 sec}, 10 pairs of Tag and control images at each PLD, total scan time 7 min. Tissue T1 and M0 were fitted using the averaged tag and control data at each PLD point. Perfusion signals were calculated by pair-wise subtraction of the tag-control series at every PLD. The perfusion data and T1 maps were then passed to a single compartment model [6] for estimating transit delay and CBF.

Figure 7:
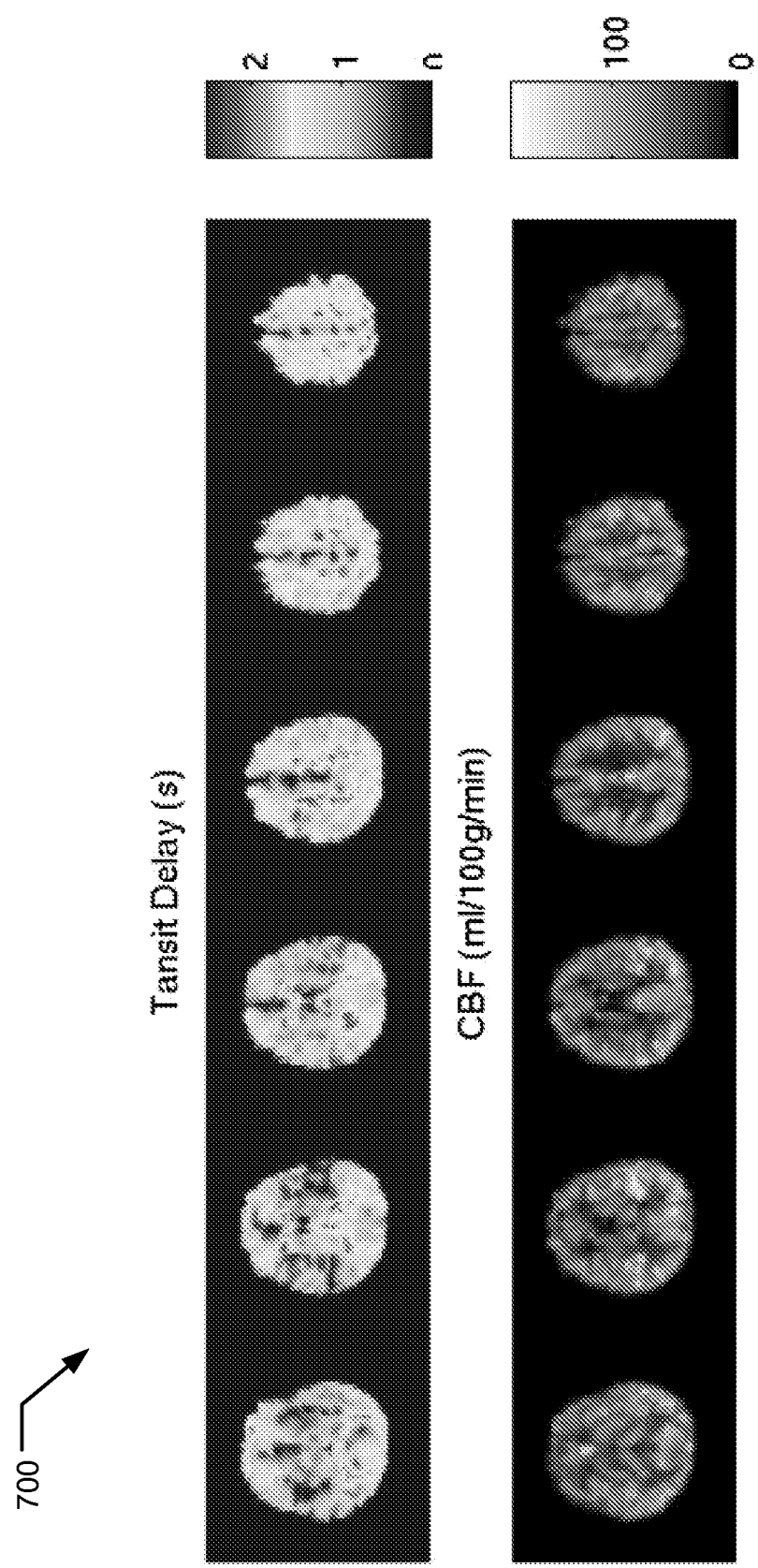
FIG. 7 shows exemplary estimated transit delay and CBF map for 6 slices.
Figure 8A:
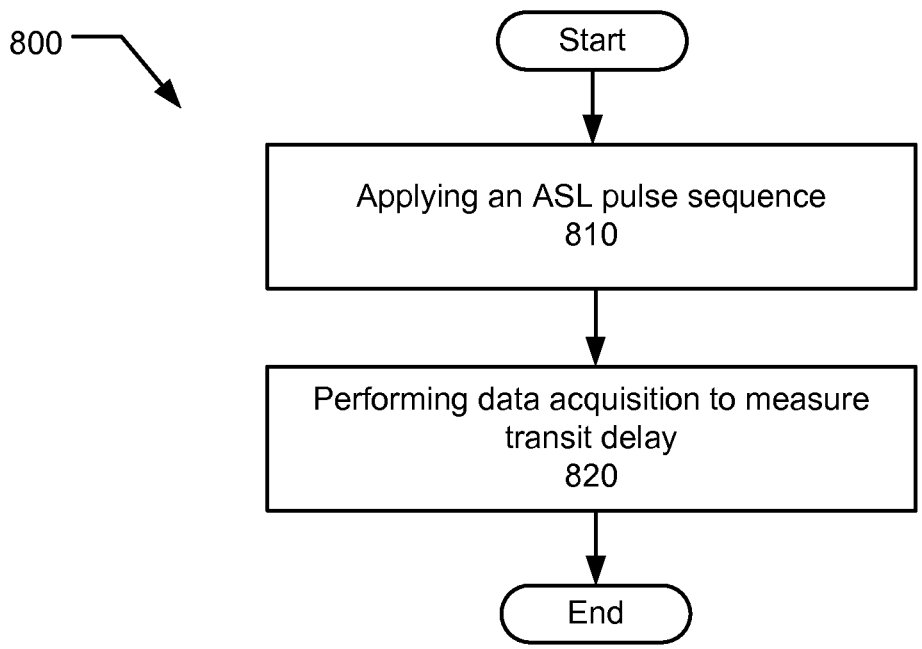
FIGS. 8A, 8B, 8C and 8D are process flow diagrams of exemplary processes for implementing an exemplary method of measuring arterial blood flow and transit delay using arterial spin labeling (ASL).
Figure 8B:
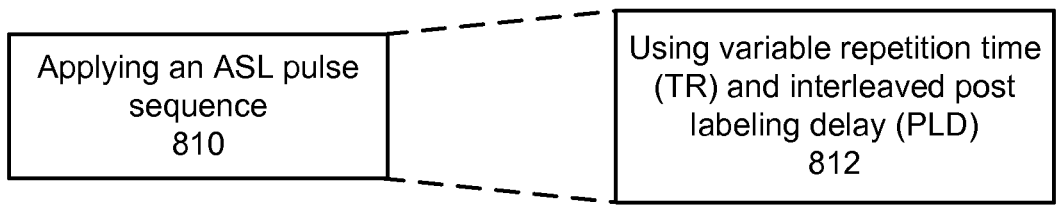
Figure 8C:
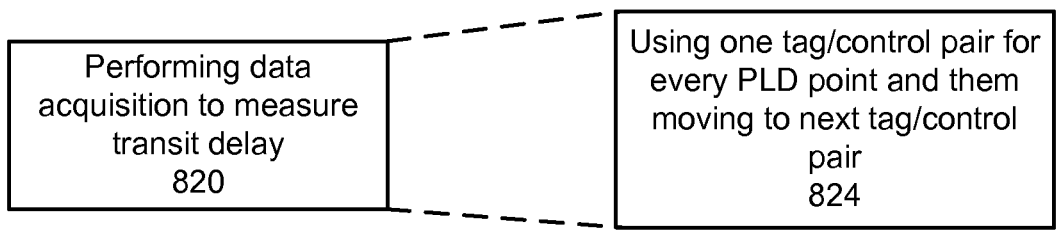
Figure 8D:
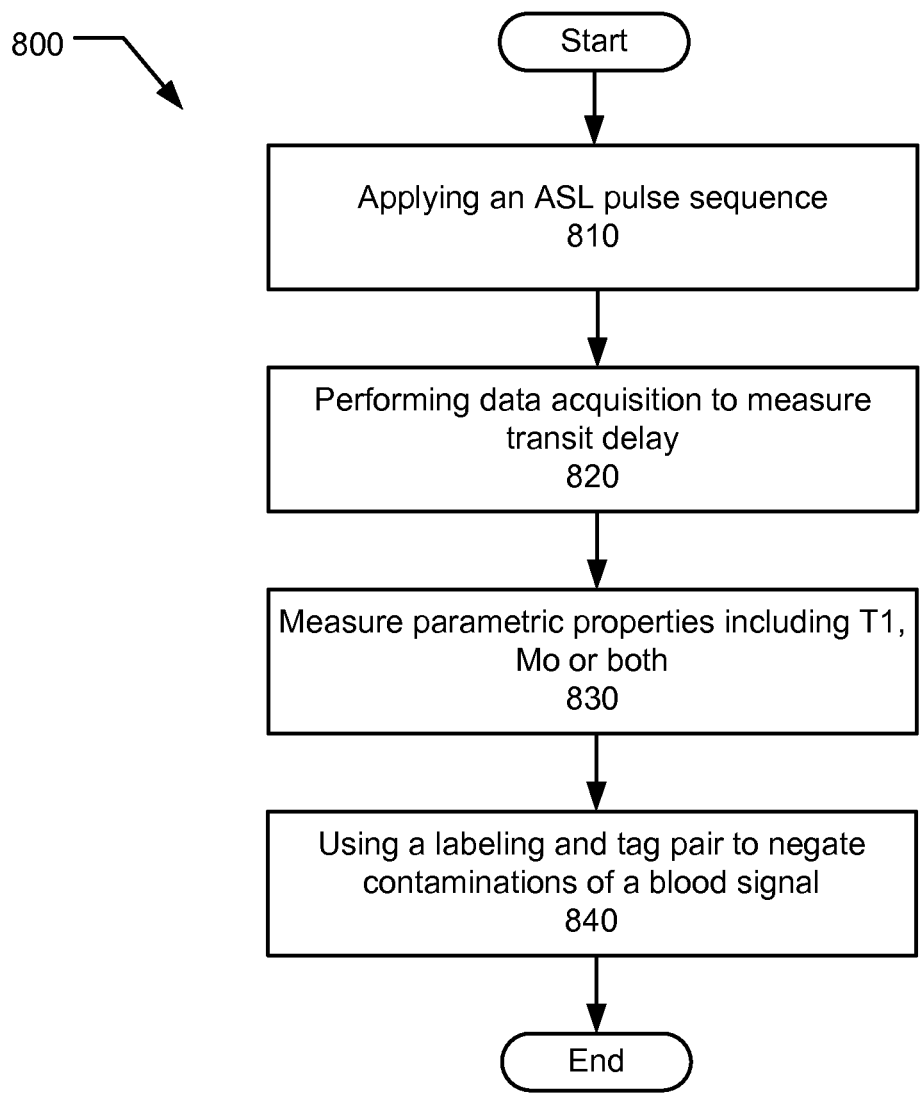

FIG. 7 shows an estimated transit delay and CBF map for 6 slices (700). The estimated mean transit delay is 0.95±0.36 sec in whole brain gray matter and 1.19±0.45 sec in white matter. The mean gray matter CBF is 79.8±35.2 ml/100 g/min and the mean white matter CBF is 49.2±25.0 ml/100 g/min, all within the typical range reported for healthy humans.

Due to inflow effects, the tissue signal at each PLD does not strictly follow a saturation recovery curve. However the error is within 1% assuming the arterial content of tissue is 1% [6]. This error is tolerable for T1 and M0 mapping. This error induced by inflow blood signal was further reduced by adding the tag and control curves in T1 and M0 estimation. The described method can also be implemented using pulsed ASL methods, such as FAIR and PICORE. The shorter labeling durations in pulsed ASL allows for a wider range of PLD values to be sampled, which should improve the accuracy of T1 estimation. However, the inferior SNR of pulsed ASL compared to PCASL mandates more averages (thus longer scan time) for reliable perfusion measurements. Test data collected using FAIR with similar parameters produced noisier estimates than the PCASL data. The described method also uses near complete saturation of imaging slice by the pre-saturation pulse 310. Partial saturation may cause the magnetization to vary from TR to TR and thus potentially induce errors in the data. Nevertheless, the described method is a simple yet effective modification of the conventional transit delay measurements. It uses shorter scan time and is less sensitive to motion. Such a method could be beneficial to all ASL studies.

FIGS. 8A, 8B, 8C and 8D are process flow diagrams of exemplary processes 800 for measuring arterial blood flow and transit delay using ASL. The process 800 includes applying an ASL pulse sequence to a target tissue (810). The ASL pulse sequence can include a pre-saturation pulse and a labeling pulse as shown in FIGS. 2B and 3 above. The pre-saturation pulse can be applied before the labeling pulse. Data acquisition is performed to measure the transit delay (820). As described with respect to FIG. 3 above, in applying the ASL pulse sequence, variable repetition time (TR) and interleaved post labeling delay (PLD) can be used (812). Also, as described with respect to FIG. 2B, one tag/control pair can be used for every PLD point and then move to the next tag/control pair (824). Also, the process can be used measure parametric properties including T1 of tissue, M0 of tissue or both (830). In addition, a labeling and tag pair can be used to negate contaminations of a blood signal within the tissue (840).

Tangible Useful Applications

The described techniques can be used for baseline CBF measurement as well as transit delay measurement. Therefore, the techniques can be a substitute for existing ASL methods, which utilize only one PLD.

Figure 9:
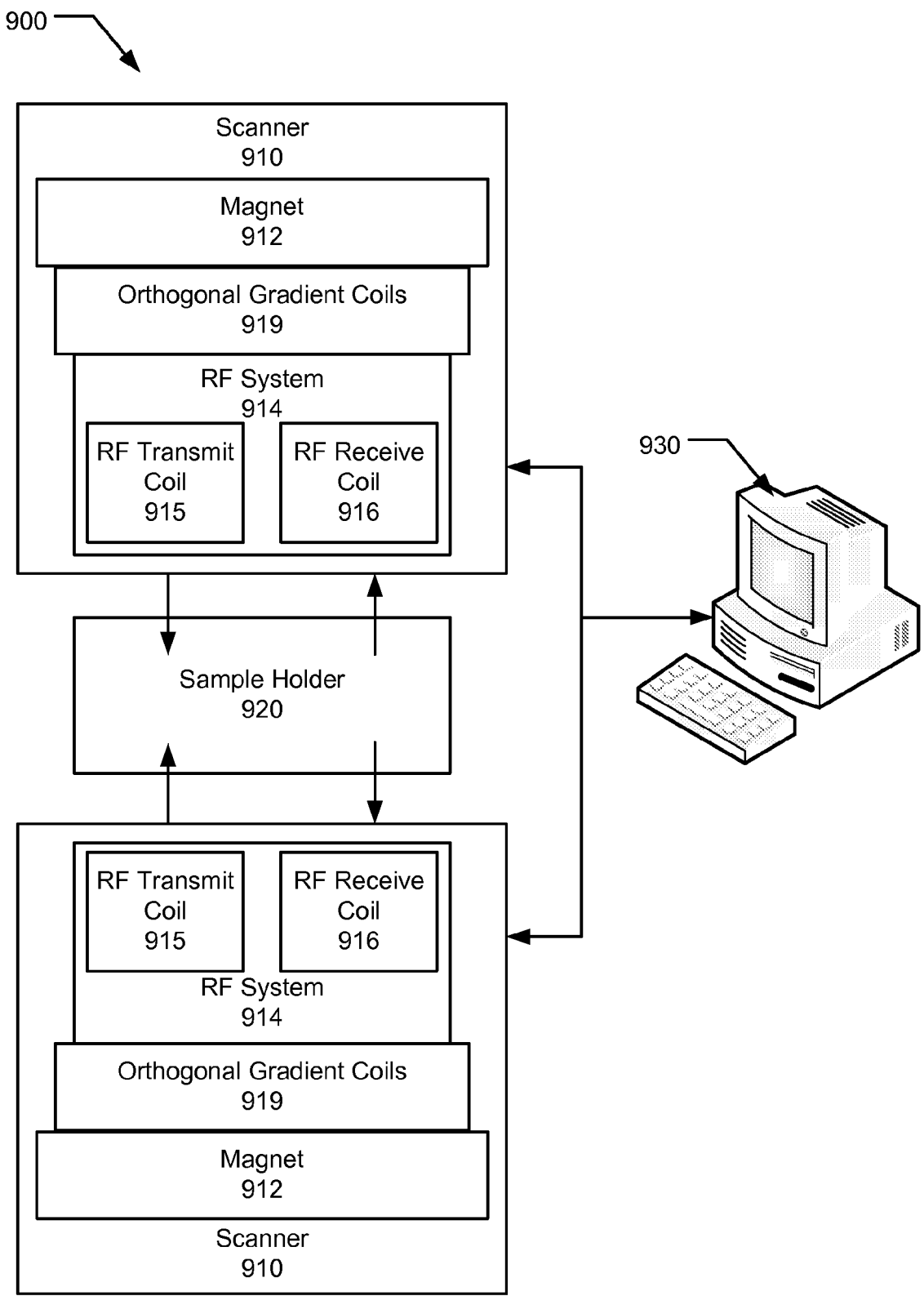
FIG. 9 shows an exemplary MRI system.

Implementations of the subject matter and the functional operations described in this specification can be implemented in various MRI machines and digital electronic circuitry, or in computer software, firmware, or hardware, including the structures disclosed in this specification and their structural equivalents, or in combinations of one or more of them. FIG. 9 shows an exemplary MRI system 900 for performing the described PCASL techniques. The MRI system 900 includes a scanner 910, a data processing apparatus 930 and a sample holder or table 925 for holding a sample 920. The scanner 910 can be implemented using any one of various MRI scanners including a General Electric (GE) Signa HDx 3.0 Tesla research scanner with a standard 8 channel head coil (GE, Waukesha, Wis.). The scanner 910 can include a main magnet 912, multiple orthogonal gradient coils 918 and a RF system 914. The main magnet 912 is designed to provide a constant, homogeneous magnetic field. The orthogonal gradient coils 918 are designed to provide three orthogonal, controller magnetic gradients used to acquire image data of a desired slice by generating an encoded and slice-selective magnetic field. The RF system 914 includes a RF transmit coil 915 and a RF receive coil designed to transmit and receive RF pulses. The RF system 945 can further include a RF synthesizer (not shown) and a power amplifier (not shown). In some implementations, an integrated transceiver coil (not shown) can be implemented instead of the separate transmit coil 915 and receive coil 916 for transmitting and receiving RF signals. For example, a close-fitting smaller coil can improve image quality when a small region is being imaged. Further, various types of coils that are placed around specific parts of a body (e.g., the head, knee, wrist, etc.) or even internally can be implemented depending on the sample and imaging applications.

The MRI system 900 is designed to perform the techniques disclosed in this specification. The RF system 914 is designed to apply to a target sample located on a sample holder 920 a non-selective inversion RF pulse, a slice-selective inversion RF pulse and a half RF excitation pulse. The three orthogonal coils 918 are designed to apply slice-selective magnetic field gradients (of a first polarity and a second polarity) and magnetic readout gradients. The data processing apparatus (e.g., a computer) 930 is designed to receive and process the acquired data to obtain desired images corresponding to the short T2 components.

Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non volatile memory, media and memory devices, including by way of example semiconductor memory devices, e.g., EPROM, EEPROM, and flash memory devices. The processor and the memory can be supplemented by, or incorporated in, special purpose logic circuitry.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Only a few implementations and examples are described and other implementations, enhancements and variations can be made based on what is described and illustrated in this application.

What is claimed is:

1. A method of magnetic resonance (MR) imaging, the method comprising:
    acquiring a succession of MR image pairs responsive to a succession of arterial spin labeling (ASL) pulse sequences, wherein each MR image pair is acquired responsive to a corresponding one of the successive ASL pulse sequences followed by a corresponding delay period;
    processing the acquired series of MR image pairs to measure arterial blood flow and transit delay of a target tissue;
    wherein acquiring the succession of MR image pairs includes:
        applying the succession of ASL pulse sequences to a labeling location in the target tissue to magnetically label arterial blood at the labeling location of the target tissue, each successive ASL pulse sequence comprising a pre-saturation pulse followed by a labeling pulse and a control pulse, and
        after applying each ASL pulse sequence, waiting a corresponding delay period different for each ASL pulse sequence before acquiring at an imaging location of the target tissue a corresponding MR image pair, wherein each MR image pair includes a labeled MR image acquired at the imaging location of the target tissue responsive to the labeling pulse that magnetically labels arterial blood and a control MR image acquired at the imaging location responsive to the control pulse that does not magnetically label arterial blood;
    wherein processing the acquired succession of MR image pairs to measure arterial blood flow includes subtracting the control MR image from the labeled MR image for each MR image pair;
    wherein processing the acquired series of MR image pairs to measure the transit delay includes processing the acquired series of MR images to identify a time period for the magnetically labeled arterial blood to transit from the labeling region to the imaging region and appear on the labeled MR images; and
    wherein a repetition time (TR) representing an amount of time between each successive ASL pulse sequence is varied.

2. The method of claim 1, wherein each successive delay period after each successive ASL pulse sequence is longer in duration.

3. The method of claim 1, wherein each successive TR is longer in duration.

4. A system for performing magnetic resonance imaging (MRI), the system comprising:
    an MRI scanner configured to:

acquire a succession of MR image pairs responsive to applying a succession of arterial spin labeling (ASL) pulse sequences, wherein each MR image pair is acquired responsive to a corresponding one of the successive ASL pulse sequences followed by a corresponding delay period; and process the acquired series of MR image pairs to measure arterial blood flow and transit delay of a target tissue;

wherein acquiring the succession of MR image pairs includes:

applying the succession of ASL pulse sequences to a labeling location in the target tissue to magnetically label arterial blood at the labeling location of the target tissue, each successive ASL pulse sequence comprising a pre-saturation pulse followed by a labeling pulse and a control pulse, and after applying each ASL pulse sequence, waiting the corresponding delay period different from other delay periods before acquiring at an imaging location of the target tissue a corresponding MR image pair, wherein each MR image pair includes a labeled MR image acquired at the imaging location of the target tissue responsive to the labeling pulse that magnetically labels arterial blood and a control MR image acquired at the imaging location responsive to the control pulse that does not magnetically label arterial blood;

wherein processing the acquired succession of MR image pairs to measure arterial blood flow includes subtracting the control MR image from the labeled MR image for each MR image pair;

wherein processing the acquired series of MR image pairs to measure the transit delay includes processing the acquired series of MR images to identify a time period for the magnetically labeled arterial blood to transit from the labeling region to the imaging region and appear on the labeled MR images; and wherein a repetition time (TR) representing an amount of time between each successive ASL pulse sequence is varied.

5. The system of claim 1, wherein each successive delay period after each successive ASL pulse sequence is longer in duration.

6. The system of claim 1, wherein each successive TR is longer in duration.

7. A non-transitory computer readable medium embodying instructions configured to cause a magnetic resonance imaging scanner to perform operations comprising:

acquiring a succession of MR image pairs responsive to a succession of arterial spin labeling (ASL) pulse sequences, wherein each MR image pair is acquired responsive to a corresponding one of the successive ASL pulse sequences followed by a corresponding delay period;

processing the acquired series of MR image pairs to measure arterial blood flow and transit delay of a target tissue;

wherein acquiring the succession of MR image pairs includes:

applying the succession of ASL pulse sequences to a labeling location in the target tissue to magnetically label arterial blood at the labeling location of the target tissue, each successive ASL pulse sequence comprising a pre-saturation pulse followed by a labeling pulse and a control pulse, and after applying each ASL pulse sequence, waiting the corresponding delay period different from other delay periods before acquiring at an imaging location of the target tissue a corresponding MR image pair, wherein each MR image pair includes a labeled MR image acquired at the imaging location of the target tissue responsive to the labeling pulse that magnetically labels arterial blood and a control MR image acquired at the imaging location responsive to the control pulse that does not magnetically label arterial blood;

wherein processing the acquired succession of MR image pairs to measure arterial blood flow includes subtracting the control MR image from the labeled MR image for each MR image pair;

wherein processing the acquired series of MR image pairs to measure the transit delay includes processing the acquired series of MR images to identify a time period for the magnetically labeled arterial blood to transit from the labeling region to the imaging region and appear on the labeled MR images; and wherein a repetition time (TR) representing an amount of time between each successive ASL pulse sequence is varied.

8. The non-transitory computer-readable medium of claim 7, wherein each successive delay period after each successive ASL pulse sequence is longer in duration.

9. The non-transitory computer-readable medium of claim 7, wherein each successive TR is longer in duration.

* * * * *